(12) United States Patent
Marcoe

(10) Patent No.: US 8,794,240 B1
(45) Date of Patent: Aug. 5, 2014

(54) APPARATUS FOR SECURING A TRACHEAL TUBE OR THE LIKE TO A PATIENT

(75) Inventor: Gregory P. Marcoe, Midland, MI (US)

(73) Assignee: Majorus Medical, Inc., Decatur, IL (US)

( * ) Notice: Subject to any disclaimer, the term of this patent is extended or adjusted under 35 U.S.C. 154(b) by 176 days.

(21) Appl. No.: 13/028,895

(22) Filed: Feb. 16, 2011

Related U.S. Application Data

(60) Provisional application No. 61/338,205, filed on Feb. 16, 2010.

(51) Int. Cl.
*A61M 16/00* (2006.01)
*A62B 9/06* (2006.01)

(52) U.S. Cl.
USPC ................. 128/207.17; 128/207.14

(58) Field of Classification Search
USPC ............ 128/207.17, 200.26, 207.14, 207.15; 604/180
See application file for complete search history.

(56) References Cited

U.S. PATENT DOCUMENTS

| | | | | |
|---|---|---|---|---|
| 3,430,300 | A | * | 3/1969 | Doan .............................. 24/304 |
| 3,834,380 | A | * | 9/1974 | Boyd ............................. 604/180 |
| 3,927,676 | A | | 12/1975 | Schultz .................... 128/207.17 |
| 4,275,721 | A | * | 6/1981 | Olson ........................... 604/180 |
| 4,598,004 | A | * | 7/1986 | Heinecke ..................... 428/41.5 |
| 4,838,868 | A | * | 6/1989 | Forgar et al. ................ 604/180 |
| 4,867,146 | A | * | 9/1989 | Krupnick et al. ............. 128/858 |
| 5,038,778 | A | | 8/1991 | Lott .......................... 128/207.17 |
| 5,042,466 | A | * | 8/1991 | McKnight ....................... 602/52 |
| 5,219,336 | A | * | 6/1993 | Wilk ............................. 604/180 |
| 5,306,233 | A | | 4/1994 | Glover ........................... 602/41 |
| 5,507,285 | A | * | 4/1996 | Mota ........................ 128/207.17 |
| 5,546,938 | A | | 8/1996 | McKenzie ............... 128/207.17 |
| 5,556,375 | A | * | 9/1996 | Ewall .............................. 602/58 |
| 5,638,814 | A | | 6/1997 | Byrd ........................ 128/207.17 |
| 7,524,307 | B2 | | 4/2009 | Davis et al. ................... 604/180 |
| 7,544,186 | B2 | | 6/2009 | Davis et al. ................... 604/180 |
| 2008/0173310 | A1 | * | 7/2008 | Marcoe .................... 128/207.17 |
| 2009/0240207 | A1 | | 9/2009 | Davis et al. ................... 604/180 |
| 2011/0015557 | A1 | * | 1/2011 | Aali et al. ....................... 602/56 |

\* cited by examiner

*Primary Examiner* — Jackie Ho
*Assistant Examiner* — Kristen Matter
(74) *Attorney, Agent, or Firm* — Alvin T. Rockhill

(57) ABSTRACT

An elongate strip of adhesive tape having an adhesive side and a non-adhesive side; (b) a first peel-away tab on and covering more than half the length of the adhesive tape; and (c) a second peel-away tabs on and covering less than half the length of the adhesive side of the adhesive tape so that when the first peel-away tab is peeled off the tape and the adhesive side of the central portion of the adhesive tape is wrapped around a tracheal tube or the like with the remaining portion of the adhesive side of the adhesive tape applied to the cheek or upper lip of the patient and then peeling the second peel-away tab from the adhesive tape and applying the thus exposed adhesive side of the adhesive tape to the other cheek or upper lip of the patient thereby securing the tube or airway to the patient. In addition, an improved kit of components for securing a tracheal tube, an adjunct tube, an oropharyngeal tube, a nasogastric tube, a laryngeal tube or a laryngeal mask airway to a patient to, the kit of components contained in a sealed and sterilizable pouch, wherein the kit includes the adhesive tape of the instant invention. Additional components of the kit may include eye tapes and tape for securing nasogastric tubes or the like to the patient.

11 Claims, 5 Drawing Sheets

APPARATUS FOR SECURING A TRACHEAL TUBE OR THE LIKE TO A PATIENT

This application claims benefit of U.S. Provisional Patent Application Ser. No. 61/338,205, filed on Feb. 16, 2010. The teachings of U.S. Provisional Patent Application Ser. No. 61/338,205 are incorporated herein by reference in their entirety.

BACKGROUND OF THE INVENTION

The instant invention relates to apparatus comprising adhesive tape for securing a tracheal tube or the like to a patient.

Various apparatus comprising adhesive tape are available for securing a tracheal tube or the like (such as an airway adjunct tube, an oropharyngeal tube, a nasogastric tube, a laryngeal tube or laryngeal mask airway) to a patient. For example, U.S. Pat. No. 3,927,676 discloses tape having a central non-adhesive portion extending around the back of the neck of the patient, the tape having bifurcated adhesive coated ends for wrapping around a tracheal tube and then attachment back to the tape to secure the tracheal tube to the patient. U.S. Pat. No. 5,038,778 and U.S. Pat. No. 5,306,233 disclose tape having a central non-adhesive portion extending around the back of the neck of the patient, the tape having bifurcated adhesive coated ends for wrapping around a tracheal tube and attachment to the patient to secure the tracheal tube to the patient. U.S. Pat. No. 5,546,938 discloses tape having a central non-adhesive portion extending around the back of the neck of the patient, the tape having bifurcated adhesive coated ends for wrapping around a tracheal tube and attachment to the upper lip to secure the tracheal tube to the patient. U.S. Pat. No. 5,638,814 discloses tape attached to central non-adhesive strap extending around the back of the neck of the patient, the tape having a central adhesive coated X-shaped portion for wrapping around a tracheal tube to secure the tracheal tube to the patient.

Despite the advances made in the art of apparatus and methods for securing a tracheal tube or the like to a patient, such apparatus and methods have not supplanted the use of un-sterilized rolls of adhesive tape even though the use of such tape may provide a means for cross-contamination and infection. Therefore, there remains a need for apparatus and methods for securing a tracheal tube or the like to a patient that are easily used and which reduce the possibility for cross-contamination and infection.

SUMMARY OF THE INVENTION

The instant invention provides an apparatus and method for securing a tracheal tube, an adjunct tube, an oropharyngeal tube, a nasogastric tube, a laryngeal tube or laryngeal mask airway to a patient. The apparatus is easily used and can be packaged in a sealed and sterilized single-use package thereby reducing the possibility for cross-contamination and infection. More specifically, the instant invention in one embodiment is an apparatus for securing a tracheal tube, adjunct tube, an oropharyngeal tube, a nasogastric tube, a laryngeal tube or a laryngeal mask airway to a patient, comprising: (a) an elongate strip of adhesive tape having an adhesive side and a non-adhesive side; (b) a first peel-away tab on and covering the adhesive side of more than half the length of the adhesive tape; and (c) a second peel-away tab on and covering the adhesive side of the remaining portion of the adhesive tape.

In another embodiment, the instant invention is an improved kit of components for securing a tracheal tube, an adjunct tube, an oropharyngeal tube, a nasogastric tube, a laryngeal tube or a laryngeal mask airway to a patient, the kit of components contained in a sealed and sterilizable pouch, wherein the improvement comprises an improved adhesive tape, comprising: (a) an elongate strip of adhesive tape having an adhesive side and a non-adhesive side; (b) a first peel-away tab on and covering the adhesive side of more than half the length of the adhesive tape; and (c) a second peel-away tab on and covering the adhesive side of the remaining portion of the adhesive tape.

In yet another embodiment, the instant invention is an improved method for securing a tracheal tube, an adjunct tube, an oropharyngeal tube, a nasogastric tube a laryngeal tube or a laryngeal mask airway to a patient using an elongate strip of adhesive tape, comprising the steps of (a) peeling a first peel-away tab on and covering the adhesive side of more than half the length of an elongate strip of adhesive tape having an adhesive side and a non-adhesive side, the adhesive tape additionally having a second peel-away tab on and covering the adhesive side of the remaining portion of the adhesive tape; (b) wrapping the adhesive side of the central portion of the thus exposed adhesive side of the adhesive tape around the tube or airway, (c) applying the remaining portion of the adhesive side of the adhesive tape of step (a) to the cheek or upper lip of the patient; (d) peeling the second peel-away tab from the adhesive tape and applying the thus exposed adhesive side of the adhesive tape to the other cheek or upper lip of the patient thereby securing the tube or airway to the patient.

BRIEF DESCRIPTION OF THE DRAWINGS

FIG. 3 is a rear view in full of a portion of the apparatus shown in FIG. 1 after the longer peel-away tab has been removed and the central portion of the apparatus is wrapped around a tracheal tube or the like;

DETAILED DESCRIPTION

Figure 1:
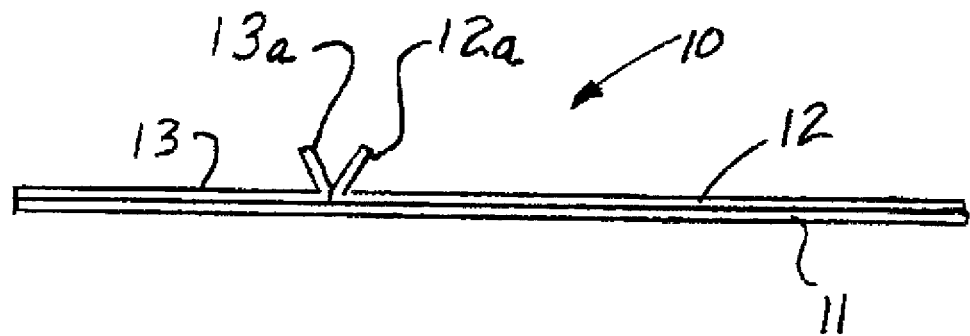
FIG. 1 is a side view in full of an apparatus embodiment of the instant invention showing two peel-away tabs on and covering the adhesive side of an elongate strip of adhesive tape.
Figure 2:
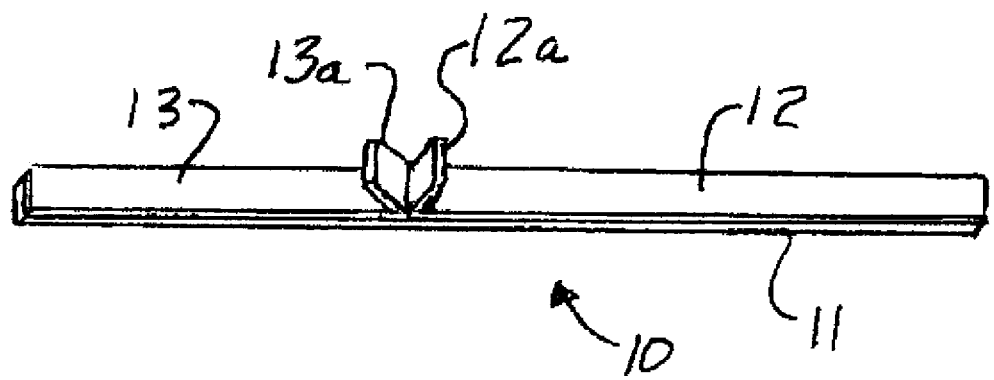
FIG. 2 is a perspective view in full of the apparatus shown in FIG. 1.

Referring now to FIG. 1, therein is shown a side view in full of an apparatus embodiment 10 of the instant invention. The apparatus 10 comprises an elongate strip of adhesive tape 11 having an adhesive side and a non-adhesive side. A second peel-away tab 13 is positioned on and covering less than half the length of the adhesive side of the adhesive tape 11. A first peel-away tab 12 is positioned on and covering more than half the length of the adhesive side of the adhesive tape 11. The pair of peel-away tabs 12 and 13 preferably have tab ends 12a and 13a so that the tabs 12 and 14 can be more easily peeled off the tape 11. Referring now to FIG. 2, therein is shown a perspective view of the apparatus 10 of FIG. 1.

Figure 3:
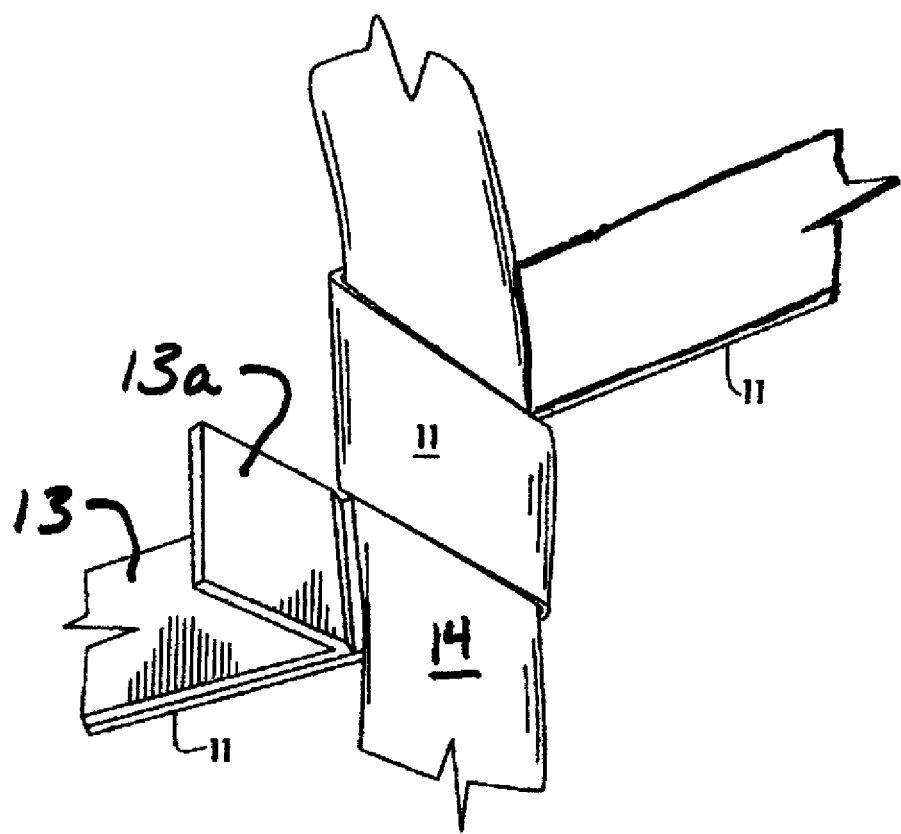
Figure 4:
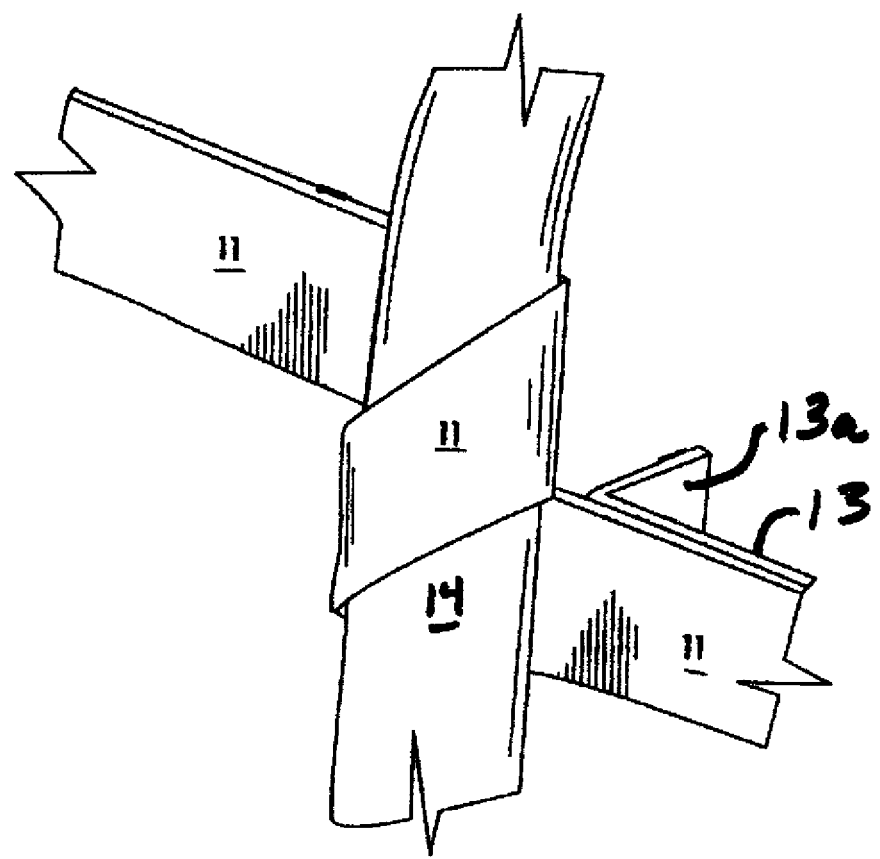
FIG. 4 is a front view in full of the system shown in FIG. 3 in position to pull the remaining peel-away tab from the tape.
Figure 5:
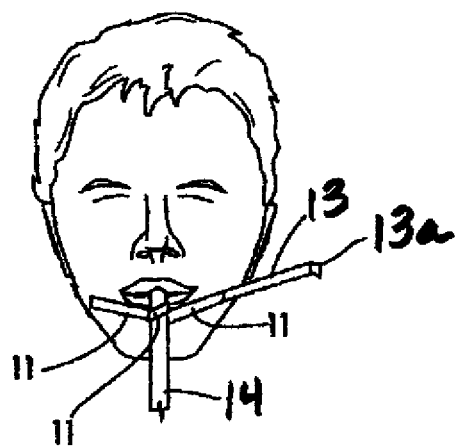
FIG. 5 is a front view in full of the system shown in FIG. 4 as the remaining peel-away tab is pulled from the tape end to adhere the tape end to the patient's cheek or upper lip.

Referring now to FIG. 3, therein is shown a rear view in full of a portion of the apparatus 10 shown in FIGS. 1 and 2 after the first peel-away tab has been removed and the central portion of the tape 11 has been wrapped around a tracheal tube 14. Referring now to FIG. 4, therein is shown a front view in full of the system shown in FIG. 3 in position to pull the remaining peel-away tab 13 from the tape 11. Referring now to FIG. 5, therein is shown front view in full of the system shown in FIG. 4 as the peel-away tab 13 is pulled from the tape 11 to adhere the remaining end of the tape 11 to the patient's cheek or upper lip thereby securing the tracheal tube to the patient.

Figure 6:
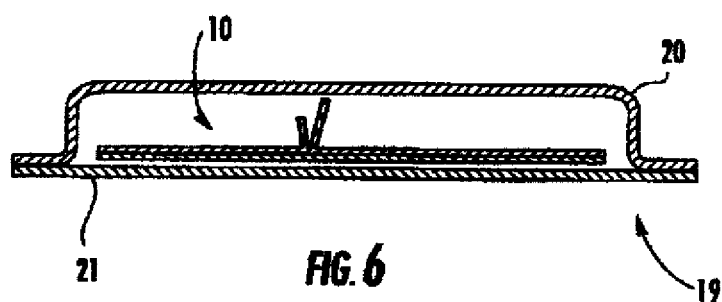
FIG. 6 is a side cross-sectional view of a kit of components for securing a tracheal tube, an adjunct tube, an oropharyngeal tube, a nasogastric tube, a laryngeal tube or a laryngeal mask airway to a patient, the kit of components contained in a sealed and sterilizable pouch and including the apparatus of FIG. 1.
Figure 7:
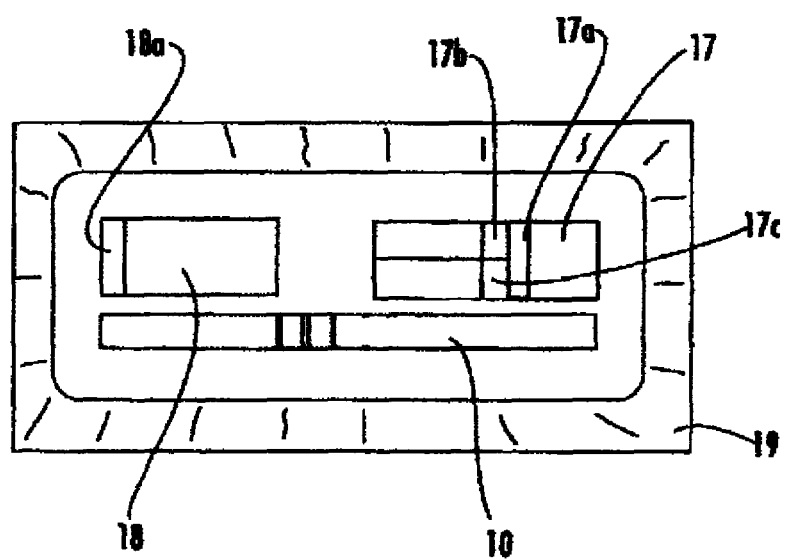
FIG. 7 is an upper view in full of the kit of components of FIG. 6 showing additional tape apparatus useful when securing a tracheal tube, an adjunct tube, an oropharyngeal tube, a nasogastric tube, a laryngeal tube or a laryngeal mask airway to a patient.

Referring now to FIG. 6, therein is shown a side cross-sectional view of a kit of components 19 for securing a tracheal tube to a patient, the kit of components contained in a conventional sealed and sterilizable pouch comprised on an upper formed transparent plastic film portion 20 sealed at the edges thereof to a lower paper portion 21, the kit 19 including the apparatus 10 of FIG. 1. Referring now to FIG. 7, therein is shown an upper view in full of the kit of components 19 of FIG. 6 showing additional tape apparatus 17 and 18 useful for securing nasogastric tubes to a patient and as eye tapes. Apparatus 17 is comprised of a piece of adhesive tape having an adhesive and non-adhesive sides and a bifurcated end. Peel-away tabs 17a, 17b and 17c are positioned on and covering the adhesive side of the adhesive tape. Apparatus 18 is simply comprised of a piece of adhesive tape having adhesive and non-adhesive sides. Peel-away tab 18a is positioned on and covering the adhesive side of the adhesive tape. The kit of components 19 can be sterilized and stored for use.

The adhesive tape used in the instant invention is preferably of the type suited for attachment to the skin, which can be sterilized by conventional means (such as exposure to ethylene oxide) and which will release the peel-away tabs without undue force. Such adhesive tape is well-known in the art. The peel-away tabs are preferably made of plastic coated paper and are also well-known in the art.

What is claimed is:

1. An apparatus for securing a tracheal tube, an adjunct tube, an oropharyngeal tube, a nasogastric tube, or a laryngeal tube to a patient, consisting of: (a) an elongate strip of adhesive tape having an adhesive side and a non-adhesive side: (b) a first peel-away tab on and covering the adhesive side of more than half the length of the adhesive tape; and (c) a second peel-away tab on and covering the adhesive side of the remaining portion of the adhesive tape, wherein the first peel-away tab and the second peel-away tab include end tabs which facilitate removal of the peel-away tabs from the adhesive side of the tape, wherein the end tab of the second peel-away tab is covered by the first peel-away tab, and wherein the apparatus is adapted to being wrapped around so as to encircle the adjunct tube, the oropharyngeal tube, the nasogastric tube, or the laryngeal tube and for securing the adjunct tube, the oropharyngeal tube, the nasogastric tube, or the laryngeal tube to the cheek or upper lip of the patient.

2. The apparatus of claim 1 wherein the end tabs extend away from the adhesive surface of the tape.

3. The apparatus of claim 1 wherein the first peel-away tab overhands the second peel-away tab.

4. The apparatus of claim 1 wherein the first peel-away tab has an essentially flat outer surface.

5. The apparatus of claim 4 wherein the flat outer surface of the first peel-away tab is in the form of a rectangle.

6. The apparatus of claim 1 wherein the end tab of the second peel-away tab extends away from the adhesive surface of the tape.

7. The apparatus of claim 1 wherein the end tab of the second peel-away tab extends toward the end of the tape which is covered by the second peel-away tab.

8. A kit for securing a tracheal tube to a patient, said kit comprising the apparatus of claim 1, and at least two strips of eye tape which are adapted for taping the eyes of said patient shut, wherein the strips of eye tape have an adhesive and a non-adhesive surface, and wherein the adhesive surface of the eye tape is completely covered with a peel-away tab, and wherein the peel away tab has tab ends which facilitate removal of the peel-away tab from the adhesive side of the eye tape.

9. The kit for securing a tracheal tube to a patient as specified in claim 8 wherein the apparatus of claim 1 and the strips of eye tape are sterilized in a sealed pouch.

10. The kit for securing a tracheal tube to a patient as specified in claim 9 wherein the apparatus of claim 1 and the strips of eye tape are sterilized in the sealed pouch by radiation treatment.

11. The kit for securing a tracheal tube to a patient as specified in claim 10 wherein the radiation treatment is by exposure to an electron beam.

* * * * *